(12) United States Patent
Kindel et al.

(10) Patent No.: US 8,994,271 B2
(45) Date of Patent: Mar. 31, 2015

(54) DEVICE FOR GENERATING A NON-THERMAL ATMOSPHERIC PRESSURE PLASMA

(75) Inventors: Eckhard Kindel, Greifswald (DE); Norbert Lembke, Greifswald (DE); Manfred Stieber, Greifswald (DE); Ruediger Titze, Greifswald (DE); Klaus-Dieter Weltmann, Binz (DE); Lutz Hellwig, Burg Stargard (DE)

(73) Assignee: Leibniz—Institut fuer Plasmaforschung und Technologie E. V., Greifswald (DE)

( * ) Notice: Subject to any disclaimer, the term of this patent is extended or adjusted under 35 U.S.C. 154(b) by 0 days.

(21) Appl. No.: 13/388,605

(22) PCT Filed: Jul. 31, 2010

(86) PCT No.: PCT/EP2010/061166
§ 371 (c)(1),
(2), (4) Date: Apr. 16, 2012

(87) PCT Pub. No.: WO2011/015538
PCT Pub. Date: Feb. 10, 2011

(65) Prior Publication Data
US 2012/0187841 A1     Jul. 26, 2012

(30) Foreign Application Priority Data

Aug. 3, 2009 (DE) .......................... 10 2009 028 190
Jun. 21, 2010 (DE) .......................... 10 2010 030 294

(51) Int. Cl.
*H01J 7/24* (2006.01)
*H05H 1/36* (2006.01)
(Continued)

(52) U.S. Cl.
CPC ................ *H05H 1/36* (2013.01); *A61B 18/042* (2013.01); *H05H 1/2406* (2013.01); *H05H 2001/2412* (2013.01); *H05H 2240/10* (2013.01); *H05H 2240/20* (2013.01)
USPC ............ 315/111.21; 315/111.51; 315/111.81; 315/111.91

(58) Field of Classification Search
USPC ........................... 315/111.01, 111.11, 111.21
See application file for complete search history.

(56) References Cited

U.S. PATENT DOCUMENTS 3,434,476 A * 3/1969 Shaw et al. ...................... 606/22
3,838,242 A * 9/1974 Goucher .................. 219/121.36
(Continued)

FOREIGN PATENT DOCUMENTS

DE    10 2006 019 664     10/2007
WO    2005 084569          9/2005

OTHER PUBLICATIONS

MEMS Wikipedia publication Dec. 2007 http://en.wikipedia.org/wiki/microelectrome.*
(Continued)

*Primary Examiner* — Douglas W Owens
*Assistant Examiner* — Srinivas Sathiraju
(74) *Attorney, Agent, or Firm* — Oblon, McClelland, Maier & Neustadt, L.L.P.

(57) ABSTRACT

A device for generating a cold, HF-excited plasma under atmospheric pressure conditions can be used advantageously for plasma treatment of materials for cosmetic and medical purposes. The device contains a metal housing functioning as a grounded electrode in the region of the emergent plasma, wherein an HF generator, an HF resonance coil having a closed ferrite core suitable for the high frequency, an insulating body acting as a gas nozzle, and a high-voltage electrode mounted in the insulating body are disposed in such a manner that they are permeated or circulated around by process gas. By integrating the plasma nozzle and required control electronics in a miniaturized handheld device, or by using a short high-voltage cable, the invention allows compliance with the electromagnetic compatibility directives and allows the power loss to be minimized and thus a mobile application to be implemented.

15 Claims, 7 Drawing Sheets

(51) Int. Cl.
*A61B 18/04* (2006.01)
*H05H 1/24* (2006.01)

(56) References Cited

U.S. PATENT DOCUMENTS

| | | | |
|---|---|---|---|
| 3,903,891 A * | 9/1975 | Brayshaw | 606/27 |
| 3,938,525 A * | 2/1976 | Coucher | 606/27 |
| 6,325,799 B1 | 12/2001 | Goble | |
| 6,676,802 B2 * | 1/2004 | Roth | 156/345.35 |
| 6,958,063 B1 * | 10/2005 | Soll et al. | 606/41 |
| 7,105,080 B2 * | 9/2006 | Mullis | 204/192.13 |
| 8,267,884 B1 * | 9/2012 | Hicks | 604/23 |
| 8,482,206 B2 * | 7/2013 | Pouvesle et al. | 315/111.21 |
| 2011/0077642 A1 * | 3/2011 | Farin | 606/34 |
| 2012/0018410 A1 * | 1/2012 | Zakrzewski et al. | 219/121.48 |

OTHER PUBLICATIONS

SMT and SMD Wikipedia Publications 2008 http://en.wikipedia.org/wiki/surface-mount_technology.*
International Search Report Issued Dec. 9, 2010 in PCT/EP10/61166 Filed Jul. 31, 2010.

* cited by examiner

DEVICE FOR GENERATING A NON-THERMAL ATMOSPHERIC PRESSURE PLASMA

BACKGROUND OF THE INVENTION

1. Field of the Invention

The invention relates to an apparatus for the production of a cold, HF-excited plasma under atmospheric pressure conditions, comprising a metal housing that functions as a grounded electrode, in the region of the exiting plasma, in which housing an HF generator, an HF resonance coil having a ferrite core suitable for the high frequency, an insulation body that functions as a gas nozzle, as well as a high-voltage electrode mounted in the insulation body are disposed in such a manner that the process gas flows around and through them. In a preferred embodiment, the apparatus comprises an electrically conductive removable cap that has a slit or a hole in the front region. The invention can advantageously be used for plasma treatment of materials for cosmetic and medical purposes. The invention makes it possible to guarantee adherence to the guidelines of electromagnetic tolerance (EMT) by means of the integration of plasma nozzle and required control electronics into a miniaturized hand-held device or by means of the use of a short high-voltage cable, and to minimize the lost power and thereby to implement mobile use.

2. Discussion of the Background

Low-temperature plasmas have already been used for quite some time for treatment of surfaces for the purpose of surface activation, etching, polymerization, layer deposition, cleaning, as well as germ reduction. At first, low-pressure plasmas in which the reactive species required for the processes can be produced, to a defined extent, by means of the selection of suitable process parameters, were primarily used for this purpose. Because low-pressure plasmas are unsuitable for numerous industrial processes both for cost reasons and for process technology reasons, alternative plasma methods were developed that work at atmospheric pressure, are therefore significantly more cost-advantageous, and can be integrated into corresponding production lines more easily. One possibility for achieving the homogeneity of the plasmas required for the ability to use atmospheric-pressure plasma methods consists in producing a plasma jet outside the discharge space, by means of a targeted disturbance of the working gas (process gas).

Applications of such jet plasmas are described in numerous patent documents. In the unexamined published patent application DE 37 33 492 A1, for example, an apparatus for production of a jet plasma is described, in which a gas stream is passed through a corona discharge segment between a rod-shaped inner electrode and a pipe-shaped outer electrode. The method described in the patent document DE 195 32 412 C2, for plasma treatment of surfaces, is based on the production of a plasma jet by means of a strong gas stream that is passed through an arc discharge segment. In this connection, various types of feed of the electrical energy can be used for production of the atmospheric-pressure discharges. For example, in the patent documents U.S. Pat. No. 6,194,036 B1 and U.S. Pat. No. 6,262,523 B1, as well as in the patent application US 2002/122896 A1, for example, arrangements are described that are based on HF excitation of atmospheric-pressure plasmas. In the sector of medicine, special HF-excited plasmas have already been used for many years for coagulation (argon plasma coagulation: U.S. Pat. No. 4,781,175 A, U.S. Pat. No. 4,060,088 A, DE 195 13 338 A1) and for HF surgery. However, in this sector, there have also been numerous more recent developments, which pursue the goal of using plasmas of this type also, for example, for coating implants to increase their biocompatibility, as well as for controlling cell adhesion on surfaces (Ohl A., Schröder K.: Plasma assisted surface modification of biointerfaces. In: Hippler R., Kersten H., Schmidt M., Schoenbach K. H. (ed.). Low Temperature Plasmas, Vol. 2. 803-820. Wiley-VCH, Weinheim 2008), for antimicrobial decontamination of surfaces (R. Brandenburg et al.: Contrib. Plasma Phys. 2007, 47, (1-2), 72-79), as well as for treatment of biological cells and tissue (I. E. Kieft et al.: IEEE Transactions on Plasma Science 2005, 33, (2), 771-775).

The invention refers to an apparatus of the type described in the patent document of the applicant, "DE 10 2006 019 664 A1". There, an easy to handle HF plasma nozzle is described, in which it is possible to do without an HF adaptation network in the form of a separate matchbox, because of the special construction. In this way, it is possible to implement an easy to handle construction of the HF plasma nozzle, which can be guided both manually and by robots.

The connection of plasma nozzle and HF generator by means of a longer cable leads to the result that the values of the electromagnetic interference radiation that occur during operation of an apparatus according to the state of the art generally exceed the limit established by the European guidelines for electromagnetic tolerance (EMT). Apparatuses of this type cannot be used without greater technical effort for ensuring adherence to these guidelines. This means that their use is restricted to applications in industrial facilities that are shielded toward the outside by means of special measures with regard to electromagnetic interference radiation. For mobile use in public areas, for example for medical, dental or cosmetic purposes, use of this apparatus is only possible if it meets the EMT requirements. It is the task of the invention to implement a plasma tool on the basis of a cold, HF-excited plasma jet that satisfies these EMT requirements and thus is suitable for mobile use in the sectors of medicine, dentistry and cosmetics. Another task consists in working in particularly gentle manner in more sensitive regions of the body. During plasma treatment, reactive species (radicals) and radiation (VUV/UV), which are important for the treatment effect, are particularly produced. For another thing, the plasma is heated as the result of loss processes, and the temperature at the tip amounts to about 50° C., which must be considered "cold" under plasma conditions. However, when used on human skin, permanent local treatment of the skin with a plasma at this temperature leads to local burns. In order to avoid such burns, the plasma is currently moved over the location to be treated at a specific speed.

Further irritation (irritation) of the skin, which expresses itself in unpleasant "tingling," is caused by the electrical current that flows from the high-voltage electrode (3) to the skin surface, by way of the conductive plasma. Normally, this is not a problem and more or less tolerable. In more sensitive regions of the body, such as in the oral cavity (in the case of treatment of the gums), for example, this is painful and cannot be defended.

SUMMARY OF THE INVENTION

The task of the invention consisted in eliminating the disadvantages of the solutions described in the state of the art. This and other objects have been achieved by the present invention the first embodiment of which includes n apparatus for the production of a cold plasma jet, comprising:

a metal housing that functions as a grounded electrode, in the region of the exiting plasma, in which housing
- a HF generator,
- a HF resonance coil having a ferrite core suitable for the high frequency,
- an insulation body that functions as a gas nozzle, as well as
- a high-voltage electrode mounted in the insulation body are disposed in such a manner that the process gas flows around and through them.

DETAILED DESCRIPTION OF THE INVENTION

According to the invention, all the modules required for operation of the plasma tool, including the HF generator, were miniaturized in such a manner that they can be integrated into a miniaturized hand-held device. In this way, a device was made available that is suitable for mobile use in the sectors of medicine, dentistry, and cosmetics. In this connection, the required direct-voltage supply can take place either from an external device or internally.

The main cause for increased electromagnetic interference radiation is the long cable connection between the plasma nozzle and an external HF generator. The advantage of the invention particularly consists in that this cable connection is eliminated by means of the integration of plasma nozzle, high-voltage coil and HF generator into an easy to handle plasma tool, and thus the problem of electromagnetic tolerance is solved, so that the technical prerequisites for approval for mobile use, for example for medical, dental and cosmetic purposes, is met. As another advantage, better handling of the plasma tool results from the miniaturization, with the tool particularly being suitable for point-accurate, local microplasma treatments. Furthermore, a further reduction in lost power is achieved by means of the invention. This has the result that heating of the plasma tool is reduced to a minimum and that the power converted in the plasma, and thus the length of the plasma jet, can be varied solely by means of regulation of the direct voltage supplied externally to the integrated HF generator.

Figure 6:
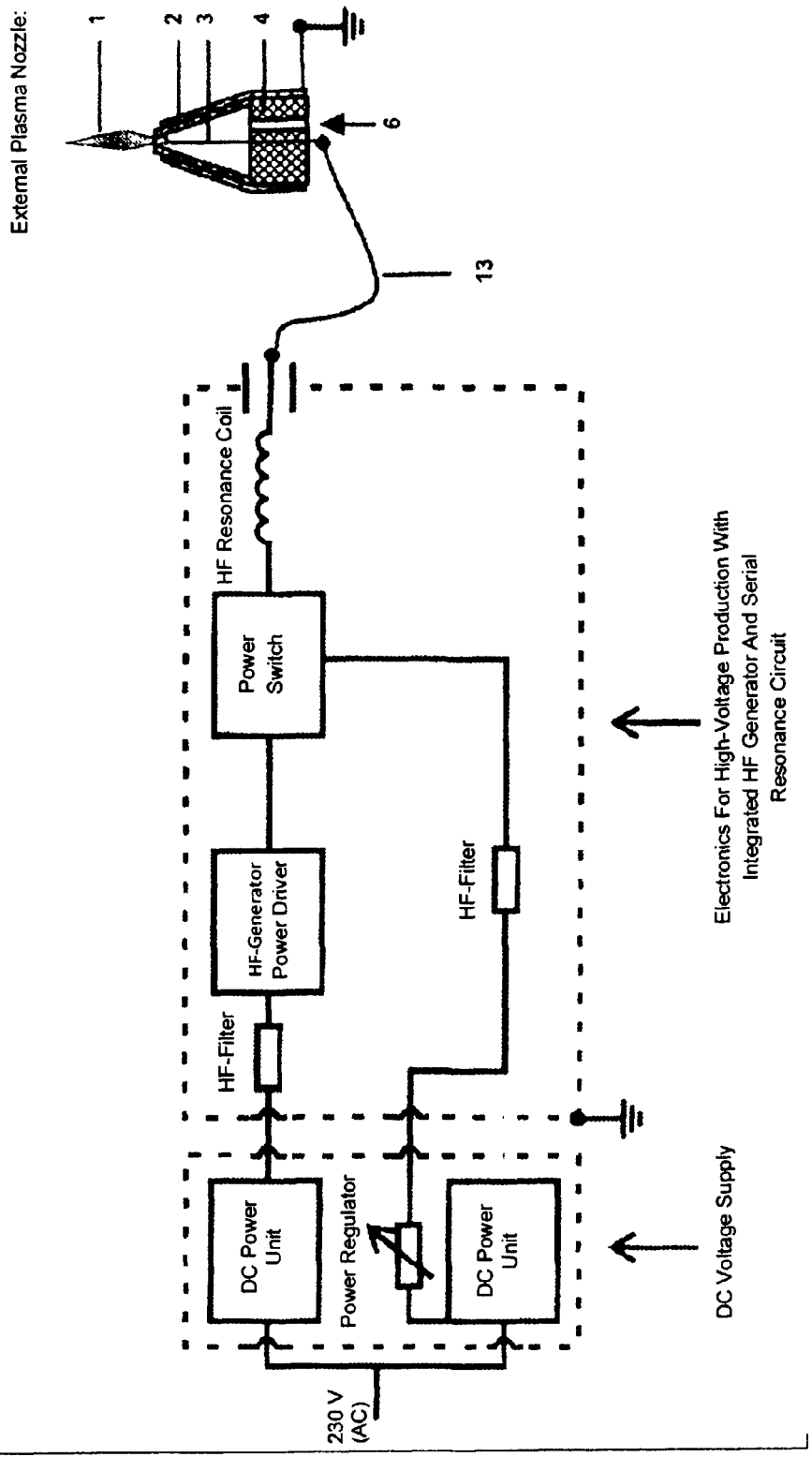
In FIG. 6, it is shown that the plasma nozzle is uncoupled from the high-voltage source and is supplied externally high-voltage cable and a corresponding process gas hose.

The alternative for the integration of plasma nozzle, high-voltage coil and HF generator consists in that, as shown in FIG. 6, the plasma nozzle is uncoupled from the high-voltage source and supplied with power externally, by way of a suitable, preferably short high-voltage cable as well as by way of a corresponding process gas hose. This arrangement makes it possible to further miniaturize the plasma nozzle and thus to be able to undertake local plasma treatment even at locations that are difficult to access. In this case, additional measures are taken to avoid increased electromagnetic interference radiation.

This arrangement furthermore offers the possibility of replacing the plasma nozzle with a different external plasma source, adapted to the object to be treated.

The production of the high-frequency voltage required for ignition of the plasma takes place in the plasma jet arrangements described in the patent document of the applicant, "DE 10 2006 019 664 A1," by way of an air coil. To shield the high frequency (adherence to EMT) as well as to hold the arrangement, the sheath generally consists of a metallic housing. The electromagnetic field generated in the air coil generates eddy currents in the metallic housing, which currents lead to undesirable inductive heating of the metal, for one thing, and must be produced by the HF generator as lost power (efficiency reduction), for another thing.

To avoid this effect, a coil having a closed ferrite core suitable for the high frequency is used in the plasma tool according to the invention, which core prevents the magnetic field generated by the coil from exiting out.

The object of the patent application is an apparatus for the production of a cold, HF-excited plasma under atmospheric pressure conditions, comprising a hollow body for the feed of a process gas, a serial resonance circuit for the production of the required high voltage, and an HF generator, characterized in that adherence to the guidelines of electromagnetic tolerance (EMT) can be guaranteed by means of miniaturization and integration of the electronic modules required for this purpose (HF generator with power driver, power switch, HF resonance coil and HF filter), and a plasma nozzle, if necessary also as a replaceable nozzle having different electrode arrangements, in an easy to handle, metallic housing, and that mobile use of the device is made possible.

According to a preferred embodiment of the invention, the apparatus comprises an electrically conductive cap (12) that has a slit or a hole (11) in the front region. The slit or the hole should have a width of at most 0.7 mm; the slit can preferably be 8 mm long. This cap is electrically connected with the housing (7) and therefore also grounded. The plasma ends in the region of the slit and cannot exit, due to the geometry of the slit, according to the principle of a Faraday cage. This cap acts like a third electrode and conducts the electrical current away to the ground. Thus, field freedom exists in the immediate vicinity of the slit.

However, the species required for therapy and the radiation stand available behind the gap, albeit in slightly reduced manner. It was possible to document the antimicrobial effect.

At the same time, the thermal energy is absorbed by this cap and the temperatures are so low that permanent treatment on the skin can take place, even in sensitive regions.

The decisive advantage is that such a removable cap represents an option for the user. If he needs a "more powerful" plasma, then he works without a cap. The cap is simply pushed on or pulled off—depending on the area of application.

The invention will be explained in greater detail below, using FIGS. 1 to 7, without being restricted to these examples.

EXEMPLARY EMBODIMENTS

The invention will be explained in detail below, using the drawings shown in FIG. 1 to FIG. 7. For identification of the individual elements of the structure of the apparatuses, the following reference symbols will be used:

| | Reference symbol list: |
|---|---|
| 1 | plasma |
| 2 | electrode (grounded housing) |
| 3 | high-voltage electrode |
| 4 | insulation body/gas nozzle |
| 5 | HF resonance coil |
| 6 | process gas |
| 7 | housing (metal) |
| 8 | HF generator/circuit board |
| 9 | DC voltage connection |
| 10 | plug-in contact |
| 11 | slit |
| 12 | cap |
| 13 | high-voltage line |
| 14 | conductive material to be treated (e.g. wire: with or without insulation) |

Figure 1:
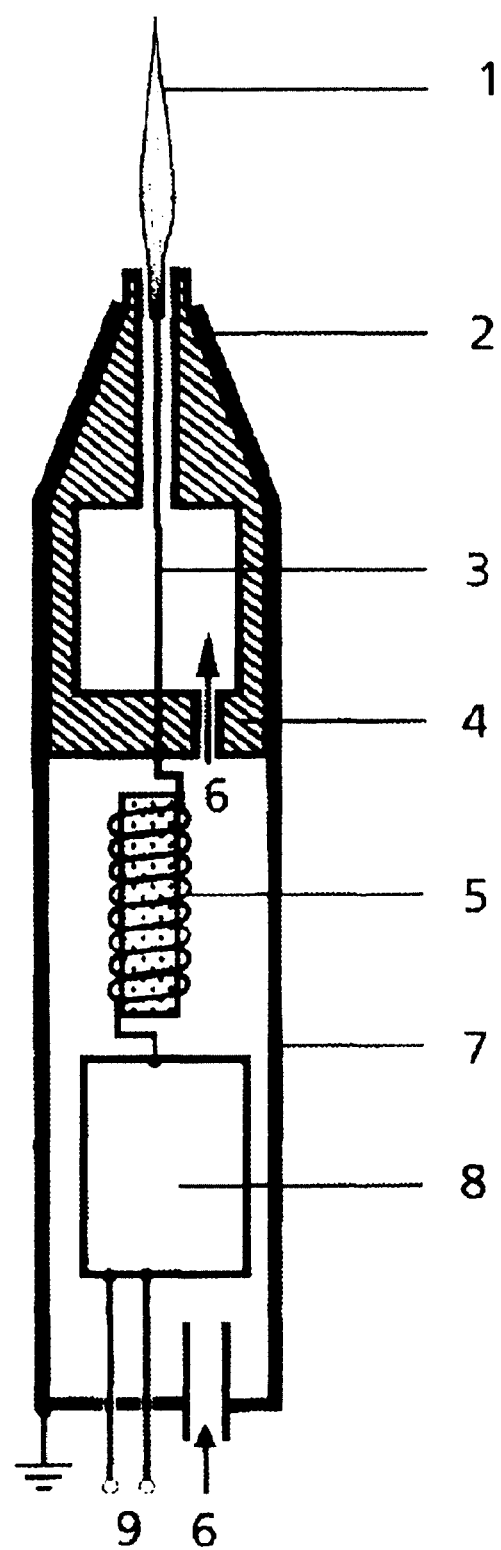
FIG. 1 shows a structure of the apparatus according to the invention, a hand-held plasma device with an integrated HF generator and serial resonance circuit.
Figure 2:
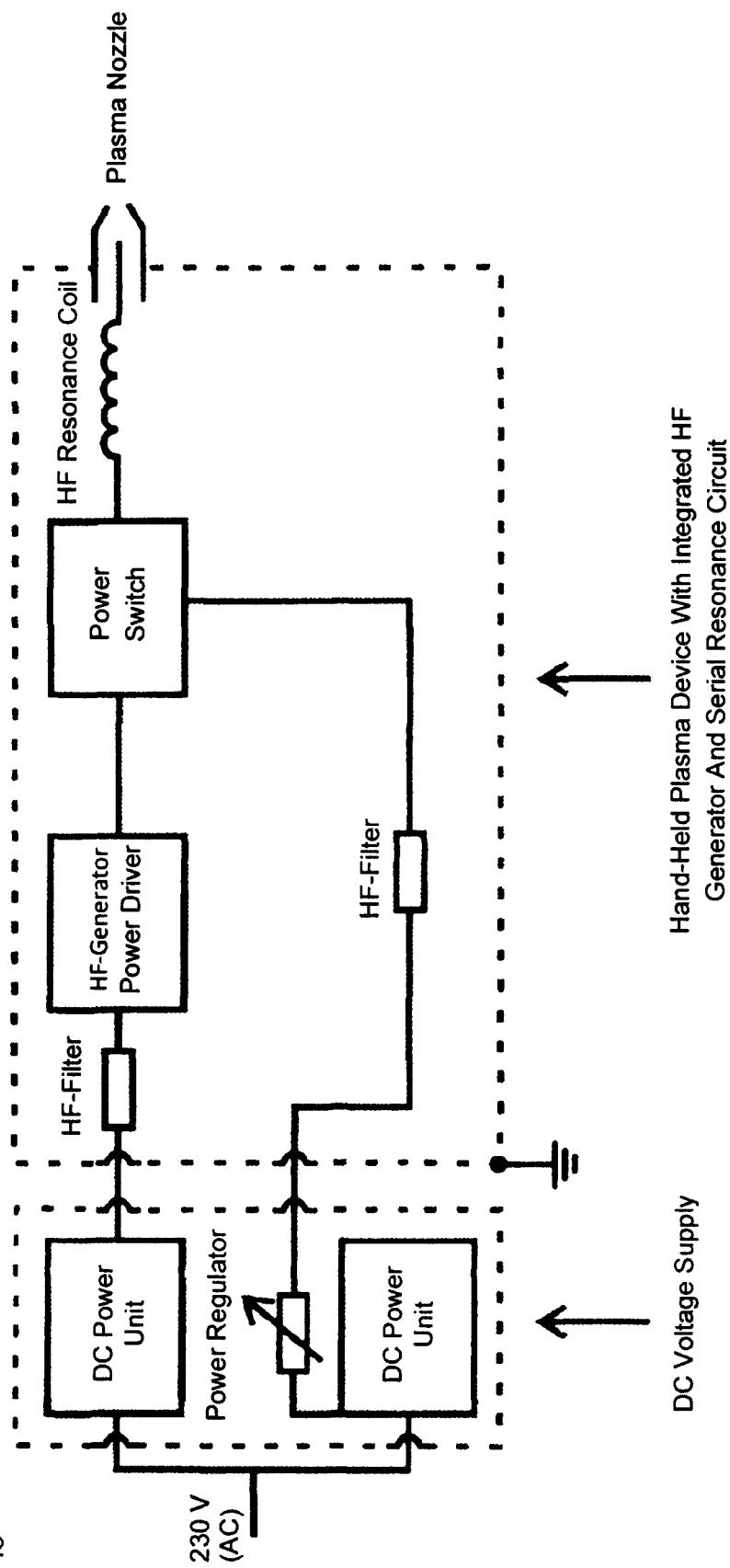
FIG. 2 shows a block schematic of an electronic circuit.

FIG. 1 shows the fundamental structure of the apparatus according to the invention, a hand-held plasma device with an integrated HF generator and serial resonance circuit. In a metal housing (7), which acts as a grounded electrode (2) in the region of the exiting plasma (1), a circuit board (8) having an EMT-appropriate board layout, an HF resonance coil (5) having a closed ferrite core suitable for the high frequency, an insulation body (4) that functions as a gas nozzle, as well as a high-voltage electrode (3) that is held in the insulation body (4) are disposed in such a manner that the process gas (6) flows around and through them. With this, the result is achieved that the flowing process gas (6) brings about cooling of the electronics (8) and the coil (5). In this connection, the circuit board (8) is preferably equipped with SMD components, in the interests of miniaturization as well as an EMT-appropriate layout. The block schematic of the electronic circuit is shown in FIG. 2. The electronic circuit implemented with the circuit board (8) consists essentially of an HF generator having a power driver for production of a suitable HF voltage having a frequency of approximately 1 MHz, and a power switch. In addition, two HF filters are used in order to avoid electromagnetic interference radiation toward the outside, by way of the feed lines to the DC voltage supply disposed outside of the hand-held plasma device.

Figure 3:
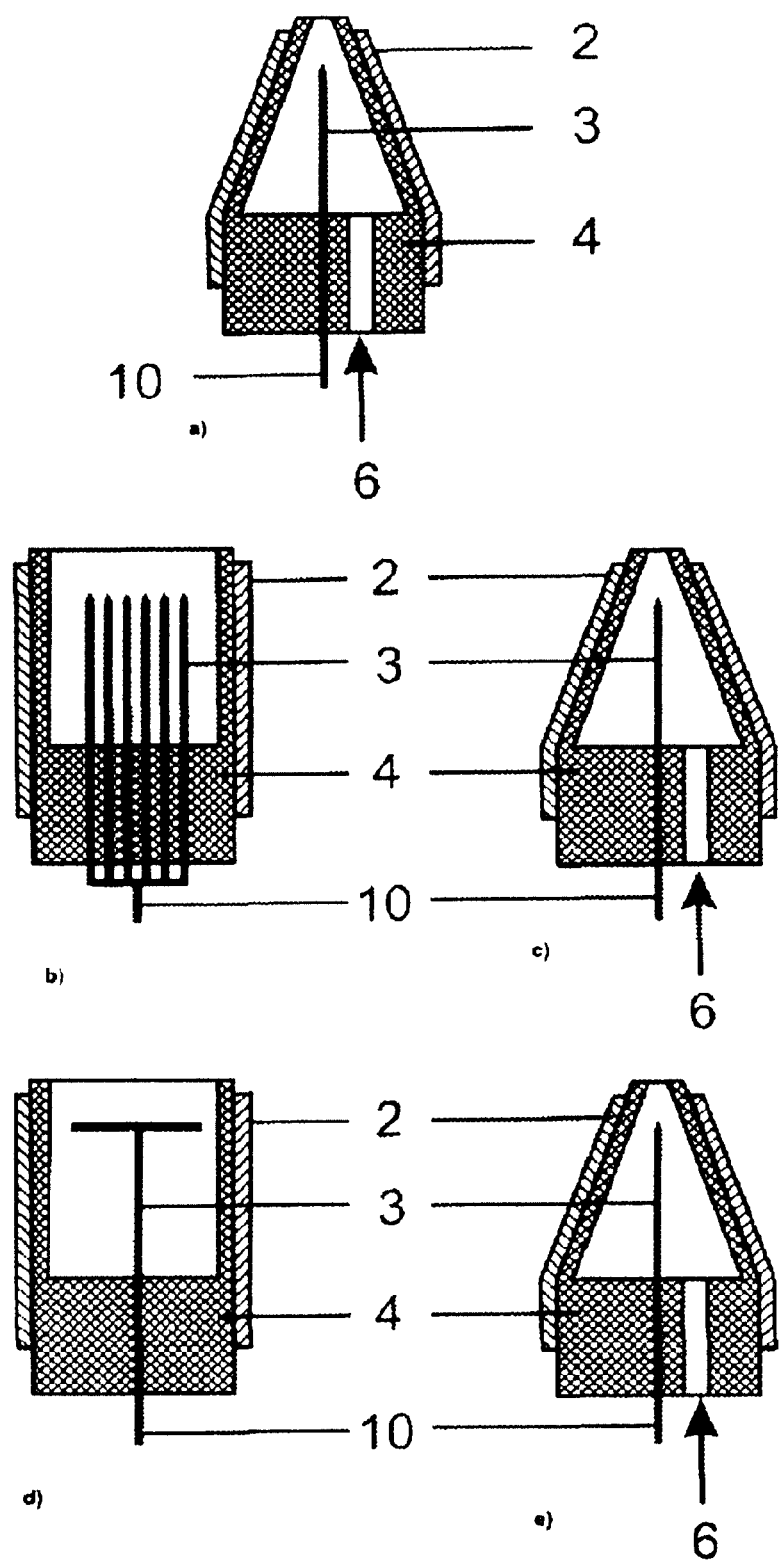
FIG. 3 shows a plasma nozzle with FIG. 3a showing a structure with a single, needle-shaped electrode and in FIGS. 3b and 3c a structure having multiple needle-shaped electrodes (FIG. 3b: front view, FIG. 3c: side view) and in FIGS. 3d and 3e a structure having a blade-shaped electrode (FIG. 3d: front view, FIG. 3e: side view).

The exemplary embodiment of the apparatus according to the invention shown in FIG. 1 is provided with a relatively small diameter, primarily for production of a single plasma jet, and is above all suitable for operation with noble gases as the process gas in this embodiment, having a gas nozzle (4) composed of insulation material. As shown in FIG. 3, in this connection, the plasma nozzle that works with an insulated, grounded electrode can be equipped with different high-voltage electrodes. Aside from the original structure with a single, needle-shaped electrode (FIG. 3a), it is possible, to widen the active plasma, to use either an arrangement having multiple needle-shaped electrodes (FIG. 3b: front view, FIG. 3c: side view) or a blade-shaped electrode (FIG. 3d: front view, FIG. 3e: side view).

Figure 4:
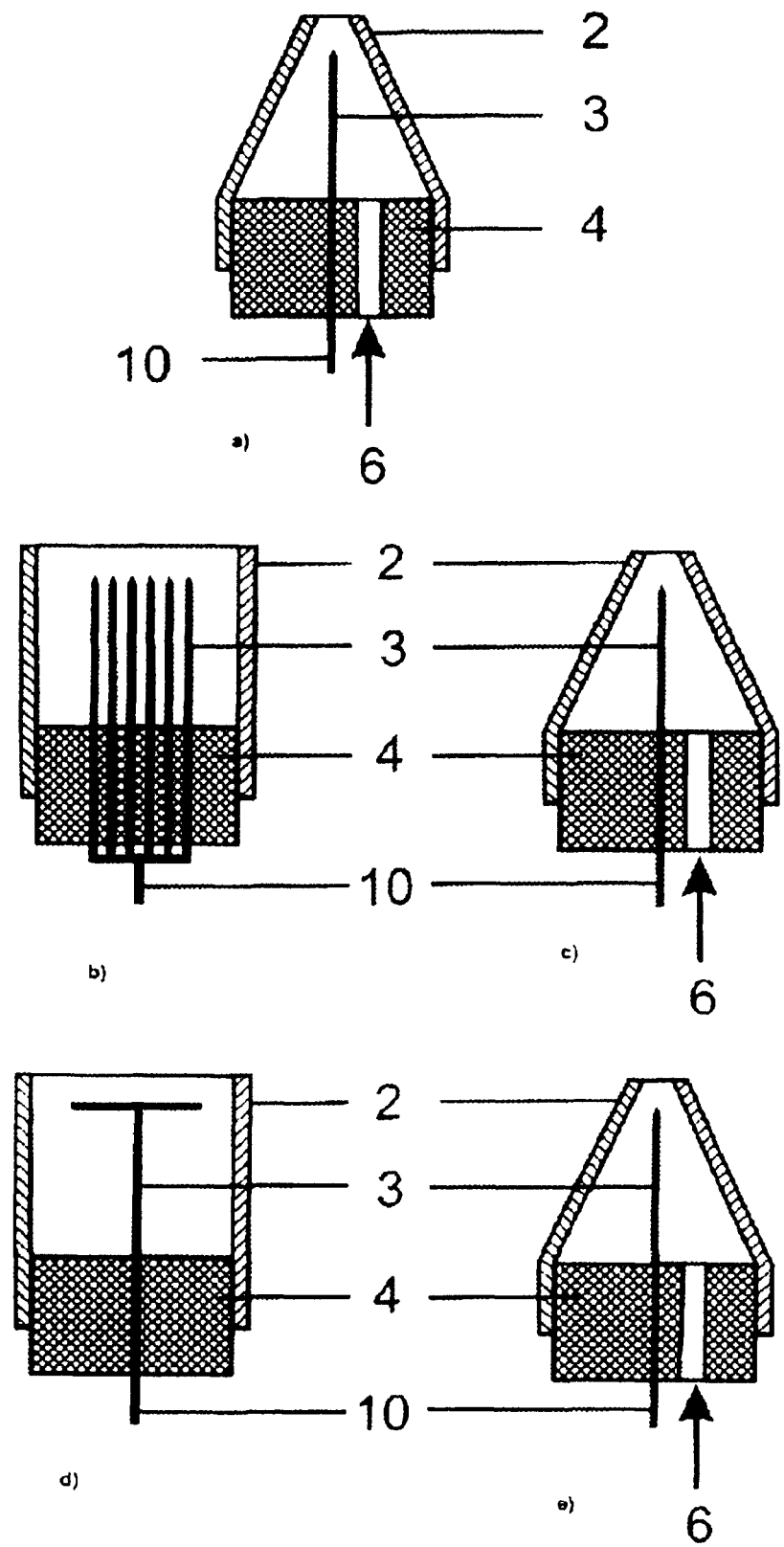
FIG. 4 shows embodiments of a plasma nozzle (FIG. 4a: nozzle with a single, needle-shaped electrode, FIG. 4b: front view of a nozzle having multiple needle-shaped electrodes, FIG. 4c: side view of a nozzle having multiple needle-shaped electrodes, FIG. 4d: front view of a nozzle having a blade-shaped electrode, FIG. 4e: side view of a nozzle having a blade-shaped electrode).

In the case of operation with molecular gases, (e.g. air or $N_2$) as the process gas, plasma nozzles are used in which the grounded electrode is not insulated relative to the gas space. Examples for embodiments of this type of plasma nozzle are shown in FIG. 4 (FIG. 4a: nozzle with a single, needle-shaped electrode, FIG. 4b: front view of a nozzle having multiple needle-shaped electrodes, FIG. 4c: side view of a nozzle having multiple needle-shaped electrodes, FIG. 4d: front view of a nozzle having a blade-shaped electrode, FIG. 4e: side view of a nozzle having a blade-shaped electrode). In this connection, the various nozzles are structured in such a manner that they are interchangeable and that the high-frequency electrodes are connected with the HF resonance coil (5) by way of a plug-in contact (10), in each instance.

Figure 5:
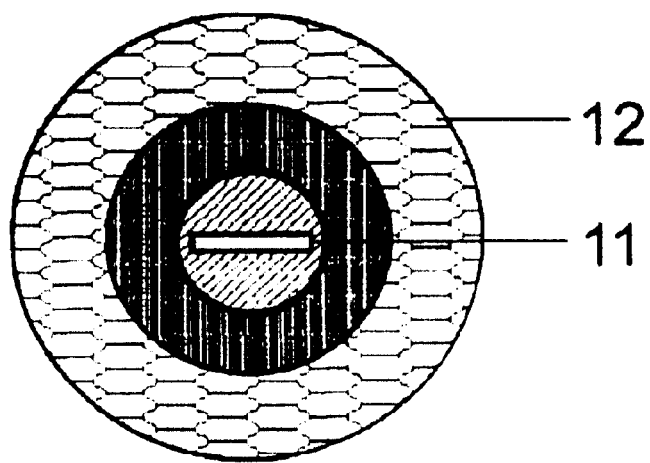
In FIG. 5, the head from FIG. 1 is shown once again.
Figure 5:
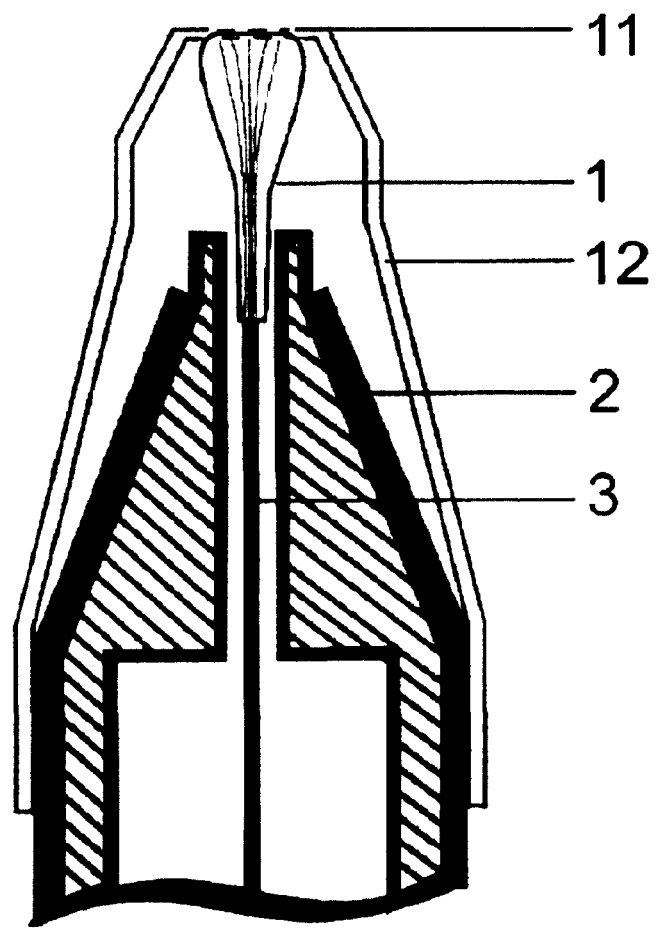

In FIG. 5, the head from FIG. 1 is shown once again. The particular embodiment as compared with the head from FIG. 1 consists of an electrically conductive cap (12), which has a slit or a hole (11) in the front region. The slit or the hole has a width of at most 0.7 mm; the slit can preferably have a length of 8 mm.

In FIG. 6, it is shown that the plasma nozzle is uncoupled from the high-voltage source and is supplied externally, by way of a suitable, preferably short high-voltage cable, as well as by way of a corresponding process gas hose.

Figure 7:
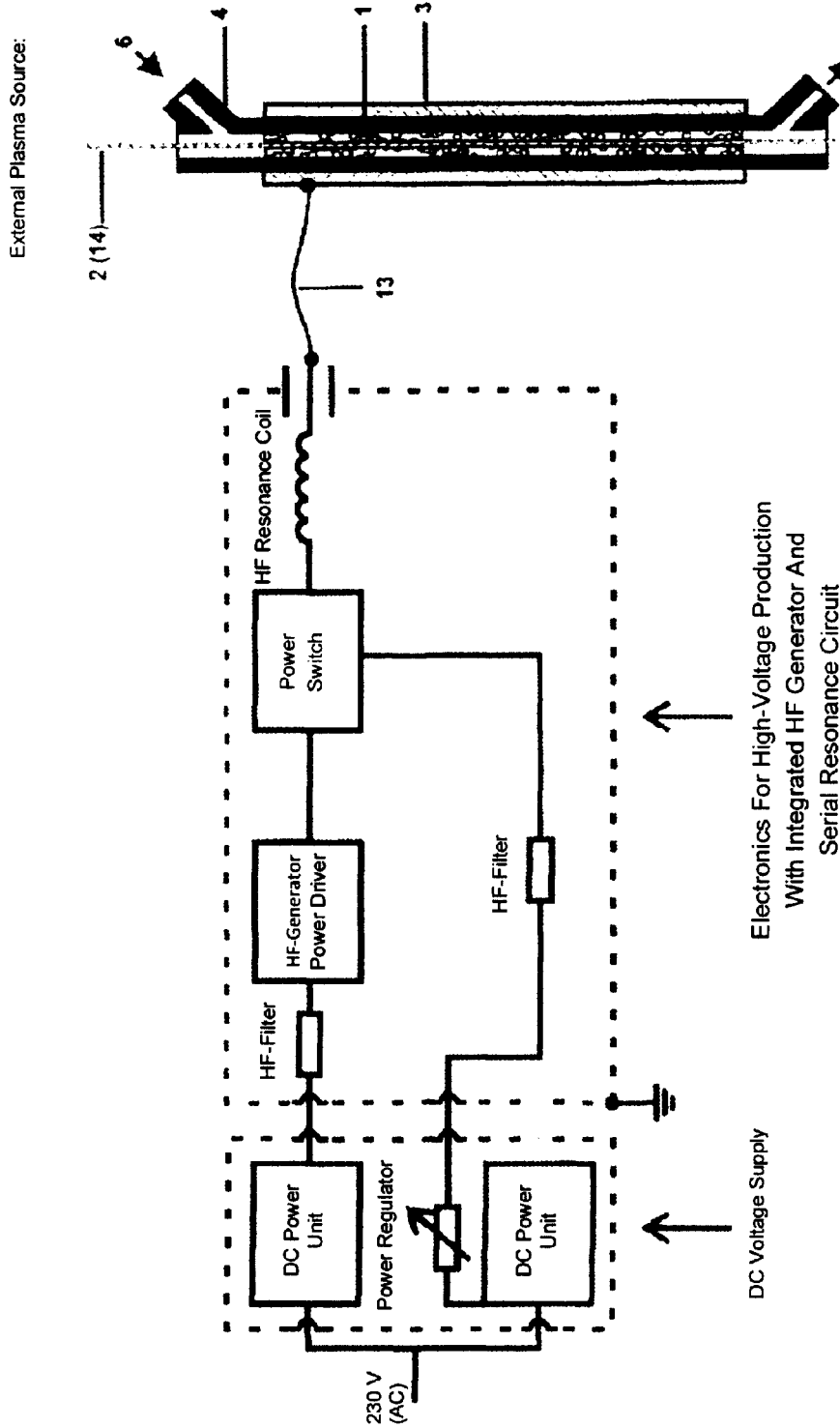
FIG. 7 shows an embodiment having a plasma source suitable for plasma treatment of insulated or non-insulated wires.

FIG. 7 shows an arrangement having a plasma source specifically suitable for plasma treatment of insulated or non-insulated wires, as an example.

The invention claimed is:

1. An apparatus for the production of a cold plasma jet, comprising:
  a mobile hand-held plasma device;
  a DC voltage supply connected to the hand-held plasma device; and
  a process gas supply connected to the hand-held plasma device;
  wherein the hand-held plasma device comprises:
  a metal housing that functions as a grounded electrode, in the region of the exiting plasma,
  a HF generator, capable of generating a high frequency of at least 1 MHz,
  a HF resonance coil having a ferrite core,
  an insulation body that functions as a gas nozzle, and
  a high-voltage electrode mounted in the insulation body, wherein
  the HF generator, the HF resonance coil and the high voltage electrode are disposed in the hand-held plasma device such that the process gas flows around them.

2. The apparatus according to claim 1, further comprising an electrically conductive removable cap, which has a slit or a hole in a front region.

3. The apparatus according to claim 2, wherein a width of the slit or the hole is at most 0.7 mm.

4. The apparatus according to claim 2, wherein the cap is electrically connected with the housing.

5. The apparatus according to claim 1, wherein the HF generator is integrated into a circuit board having an EMT-appropriate board layout.

6. The apparatus according to claim 5, wherein the circuit board comprises a power driver for the production of a HF voltage having a frequency of approximately 1 MHz and a power switch.

7. The apparatus according to claim 1, which further comprises an HF filter.

8. The apparatus according to claim 1, wherein the process gas comprises a gas selected from the group consisting of a noble gas, air, oxygen, and nitrogen.

9. The apparatus according to claim 1, wherein the high-voltage electrode is a single, needle-shaped electrode or a blade-shaped electrode, or multiple needle-shaped electrodes serve as the high-voltage electrode.

10. The apparatus according to claim 1, comprising interchangeable gas nozzles; wherein the high-voltage electrodes are connected with the HF resonance coil with a plug-in contact.

11. The apparatus according to claim 1, wherein when the process gas is a molecular gas, the grounded electrode is not insulated relative to a gas space.

12. The apparatus according to claim 1, which comprises a battery.

13. The apparatus according to claim 1, wherein the gas nozzle is capable of being uncoupled from the high-voltage source and capable of being supplied externally with a high-voltage cable.

14. The apparatus according to claim 11, wherein the molecular gas is air or nitrogen.

15. The apparatus according to claim 5, wherein the apparatus is configured to cool the circuit board by flowing the process gas around it.

* * * * *